United States Patent [19]

Montalto et al.

[11] 4,296,070
[45] Oct. 20, 1981

[54] SLIDE DISTRIBUTOR FOR A CHEMICAL ANALYZER

[75] Inventors: Michael S. Montalto; Douglass L. Blanding; Michael R. Smith, all of Rochester, N.Y.

[73] Assignee: Eastman Kodak Company, Rochester, N.Y.

[21] Appl. No.: 159,564

[22] Filed: Jun. 16, 1980

[51] Int. Cl.³ .............................................. G01N 35/04
[52] U.S. Cl. ........................................ 422/65; 422/64
[58] Field of Search ..................... 23/230 R, 230 B; 422/64-66; 424/3; 353/113; 119/35, 39, 43; 435/809

[56] References Cited

U.S. PATENT DOCUMENTS

| 2,260,660 | 10/1941 | Darwin | 88/28 |
| 3,485,558 | 12/1969 | Michniewicz | 353/104 |
| 3,574,454 | 4/1971 | Deeg | 353/114 |
| 3,650,437 | 3/1972 | Binnings et al. | 222/136 |
| 3,656,846 | 4/1972 | Hipelius et al. | 353/104 |
| 3,659,934 | 5/1972 | Costanza et al. | 353/103 |
| 3,992,158 | 11/1976 | Przybylowicz et al. | 23/253 TP |
| 4,018,521 | 4/1977 | Mischenko | 353/104 |
| 4,053,381 | 10/1977 | Hamblen et al. | 204/195 M |
| 4,152,390 | 5/1979 | Nosco et al. | 422/63 |
| 4,219,529 | 8/1980 | Tersteeg et al. | 422/65 |
| 4,224,032 | 9/1980 | Glover et al. | 422/65 |

Primary Examiner—Ronald Serwin
Attorney, Agent, or Firm—Donald D. Schaper

[57] ABSTRACT

A slide distributor is disclosed for transferring analysis slides between a plurality of modular elements in a chemical analyzer. The distributor comprises a rotor having a plurality of radial arms each of which has a slide holder adapted to receive an analysis slide and to transport the slide to a selected location in the analyzer. The slide holders are adapted to interact with locating means at each of the elements to facilitate the processing of the slides and transfer of the slides between the elements.

14 Claims, 6 Drawing Figures

SLIDE DISTRIBUTOR FOR A CHEMICAL ANALYZER

CROSS-REFERENCE TO A RELATED APPLICATION

Reference is made to commonly-assigned U.S. Patent Application Ser. No. 857,344, entitled: Method and Apparatus for Chemical Analysis, filed in the name of Glover et al. on Dec. 5, 1977, and now U.S. Pat. No. 4,224,032.

BACKGROUND OF THE INVENTION

1. Field of the Invention

This invention relates to apparatus for the chemical analysis of substances, and more particularly to a mechanism for delivering an analysis slide to a plurality of modular elements in a chemical analyzer.

2. State of the Prior Art

Recent developments have provided analysis slides for use in performing quantitative analyses of biological fluids. The slides are essentially planar, contain reagents in dry form, and can be loaded into a cartridge for use in a chemical analyzer. In the operation of such an analyzer, an analysis slide is fed from a cartridge into a metering station where a predetermined amount of sample fluid is deposited on the analysis slide. After an appropriate incubation period, the slide is moved to an analysis station where a change in the slide is sensed, the amount of change being proportional to a particular analyte in the sample fluid. The slide is used only once and is discarded after the reading has been taken. An analyzer for use with slides of this type is described in commonly-assigned U.S. Pat. No. 4,152,390, granted on May 1, 1979.

There is a growing trend in the clinical apparatus field toward analyzers which include a plurality of removable modules. The use of modules permits an analyzer to be easily modified to fit the needs of a particular user, and it also facilitates maintenance of the analyzer in that modules can be exchanged rather than repairing a module on the analyzer. In such apparatus, there is a problem in insuring that the modules installed on the apparatus are properly aligned with other apparatus elements which interfere with the modules. The alignment problem is especially critical when relatively small, light objects must be transferred from one module to another. Although it is possible to align the various modules of an analyzer by a trial-and-error method, this is very time consuming; further, the modules can become misaligned during operation of the analyzer due to wear and vibration.

Slide handling apparatus is known in clinical apparatus for transferring slides between permanently mounted elements of the apparatus. For example, the patent to Binnings et al., U.S. Pat. No. 3,650,437, discloses apparatus having a slide distributor in the form of a turntable which is adapted to advance slides through a series of stations in the apparatus. The turntable comprises a plurality of pivotally mounted slide holders spaced around its outer periphery. At certain points in the operating cycle, the slide holders engage a fixed ramp, or cam, which pivots the slide holder and the slide carrier thereon to an angular position in which certain operations are performed on the slide. There is no suggestion, however, in the Binnings et al. patent of a solution to the problem of aligning a slide transport device with removable modular elements.

Slide handling mechanisms are also found in the photographic art, although none of the known mechanisms include means for transferring slides between removable modules. Representative of the mechanisms in the photographic art is the patent to Costanza et at., U.S. Pat. No. 3,659,934, which discloses a slide projector having a slide supply magazine supported above a turntable. Slides are fed from the magazine onto the turntable which moves the slides into a position for projection; after projection, the turntable moves the slides into a receiving chamber where the slides are collected for eventual restacking in a supply magazine.

SUMMARY OF THE INVENTION

It is an object of the invention to overcome the above-described problems of prior-art devices and to provide a novel and improved sllide distributor for transporting analysis slides through an analyzer having a plurality of modular elements. This invention is particularly suitable for use in an analyzer in which the fluid is metered onto a generally planar, dry analysis slide which is analyzed after an appropriate period of incubation.

In accordance with one aspect of the invention, there is provided apparatus for use in measuring a characteristic of a sample fluid wherein the fluid is deposited on an analysis slide which is analyzed after an appropriate period of time, the apparatus comprising: a plurality of apparatus elements, the elements being arranged in a preselected sequence along a path traveled by the slide in the apparatus, the elements including slide supply means, metering means for depositing a predetermined quantity of sample on a slide supported in a metering position, and incubator means; slide transfer means for moving a slide from the slide supply means along the slide path and for delivering a slide to a selected one of the elements; drive means for moving the slide transfer means through a series of slide advance cycles; and locating means engageable with the slide transfer means for precisely positioning the slide transfer means and a slide therein relative to each of the elements each advance cycle to facilitate the processing of the slides and the transfer of slides between the elements and the transfer means.

In a preferred embodiment of the invention, the slide transfer means includes a rotor which is mounted in a central location in the apparatus and is adapted to deliver a slide to a plurality of elements, or modules, in the analyzer. In operation of the apparatus, the transfer means receives an analysis slide from one of a pair of slide supply means, moves the analysis slide to a metering position where a predetermined amount of fluid is deposited on the slide, and then deposits the analysis slide in a selected one of a pair of incubators. Analysis means operatively associated with the incubators are adapted to measure a change in the analysis slide as a result of fluid deposited thereon.

The rotor includes a plurality of radially-extending arms, each of which has a slide holder located at its outer end for receiving an analysis slide to be processed. The slide holder is supported on the rotor arm by means of a plurality of flexure members which permit vertical movement of the slide holder within preselected limits. At each of the analyzer elements, a ramp cooperates with the slide holder to precisely locate the slide holder in a vertical position relative to the analyzer element. A movable stop serves to locate the rotor in a circumferential position, and a roller mechanism positions the analysis slide along the radius of the rotor just prior to movement of the slide into the metering position. A drive means is provided for advancing the rotor in angular increments of a predetermined amount.

The slide distributor disclosed herein is intended for use on a high-speed analyzer which is adapted to process a large number of analysis slides per hour. An important element of the invention is the means for precisely locating the slide distributor relative to the analyzer elements such that the elements can properly interface with the analysis slides, thereby insuring that slide jams do not occur. The means for locating the slide distributor is particularly advantageous for use with analyzer elements in the form of removable modules.

DESCRIPTION OF THE PREFERRED EMBODIMENT

The invention is described hereinafter in connection with an analyzer for performing quantitative chemical analyses of biological fluids, such as blood serum. However, the invention is not so limited, and it can also be employed in other types of apparatus where objects must be transferred from station to station and accurately located in each of the stations.

The invention is useful with analyzers in which the substrate which makes the test possible comprises a pair of electrodes selective to the ion activity of choice. Recent developments have provided the electrodes in essentially planar, dry form suitable for use in pairs in an analyzer. An example of such a test element is disclosed in the patent to Hamblen et al., U.S. Pat. No. 4,053,381, granted on Oct. 11, 1977. This patent describes a test element, or analysis slide, of the type which is used to potentiometrically designate the activity of ions in a liquid test solution.

The invention can also be used with other forms of test elements, as for example, the element disclosed in the commonly-owned patent to Przybylowicz et al., U.S. Pat. No. 3,992,158, granted on Nov. 16, 1976. The test element disclosed in this patent is formed as a multilayered element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid.

Terms such as "up," "down," "lower," "vertical," "horizontal," and "bottom," as used herein, refer to the orientation of parts when the apparatus is positioned in its customary position of use.

Figure 1:
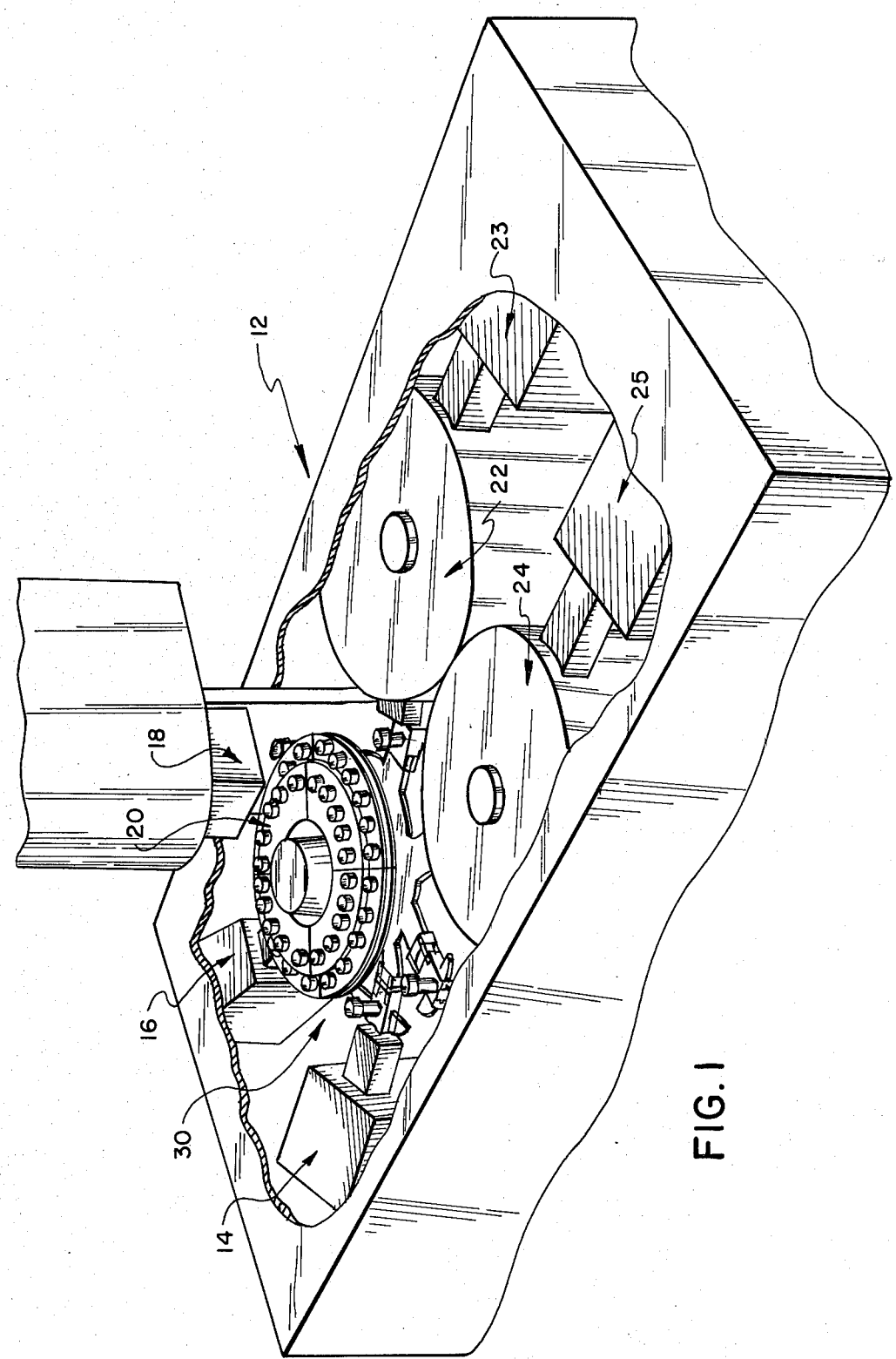
FIG. 1 is a perspective view of a chemical analyzer of the type which is adapted to employ the slide distributor described herein.

In accordance with the preferred embodiment of the invention, there is shown in FIG. 1 an analyzer 12 of the type which is adapted to employ a slide distributor 30 as described herein. Analyzer 12 comprises a slide supply 14 for analysis slides 15 of the colorimetric type (FIG. 3) and a slide supply 16 for analysis slides 17 of the potentiometric type. A metering device 18 is adapted to meter sample fluid from a cup 19 in sample tray 20 (FIG. 2) onto an analysis slide 15 or 17 in slide distributor 30. A second metering device, not shown, works in conjunction with metering device 18 to also deposit reference fluid on analysis slides 17. After the metering operation, analysis slides 17 of the potentiometric type are delivered by distributor 30 to an incubator 22, and analysis slides 15 of the colorimetric type are delivered to an incubator 24. Incubators 22, 24, are adapted to cooperate respectively with analysis means 23, 25, (FIG. 1) for measuring changes in the analysis slides 17, 15, as a result of the fluid deposited thereon. As will be described in more detail hereinafter, means are provided for precisely locating the slide distributor 30 and the slides 15, 17, held therein relative to analyzer elements during the processing and transporting of the slides.

As noted above, apparatus 12 is adapted to process both slides 17 of the potentiometric type and slides 15 of the colorimetric type. (See FIG. 3.) However, in order to simplify the following discussion of the slide distributor 30, only analysis slide 15 will be referred to when the particular operation being discussed can be performed on either slide 15 or slide 17.

Figure 2:
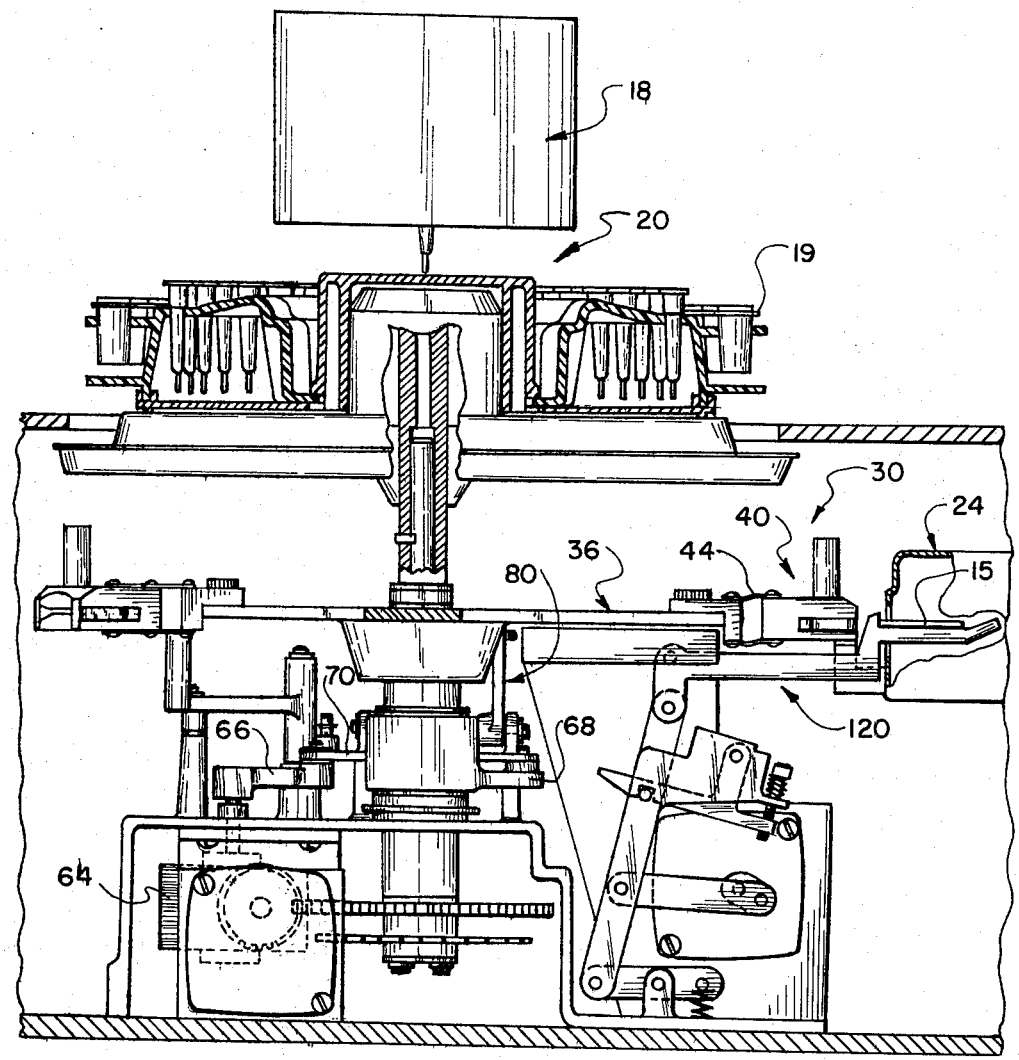
FIG. 2 is a fragmentary elevational view, partially in section, of the slide distributor, drive means for the slide distributor, and the sample tray.
Figure 3:
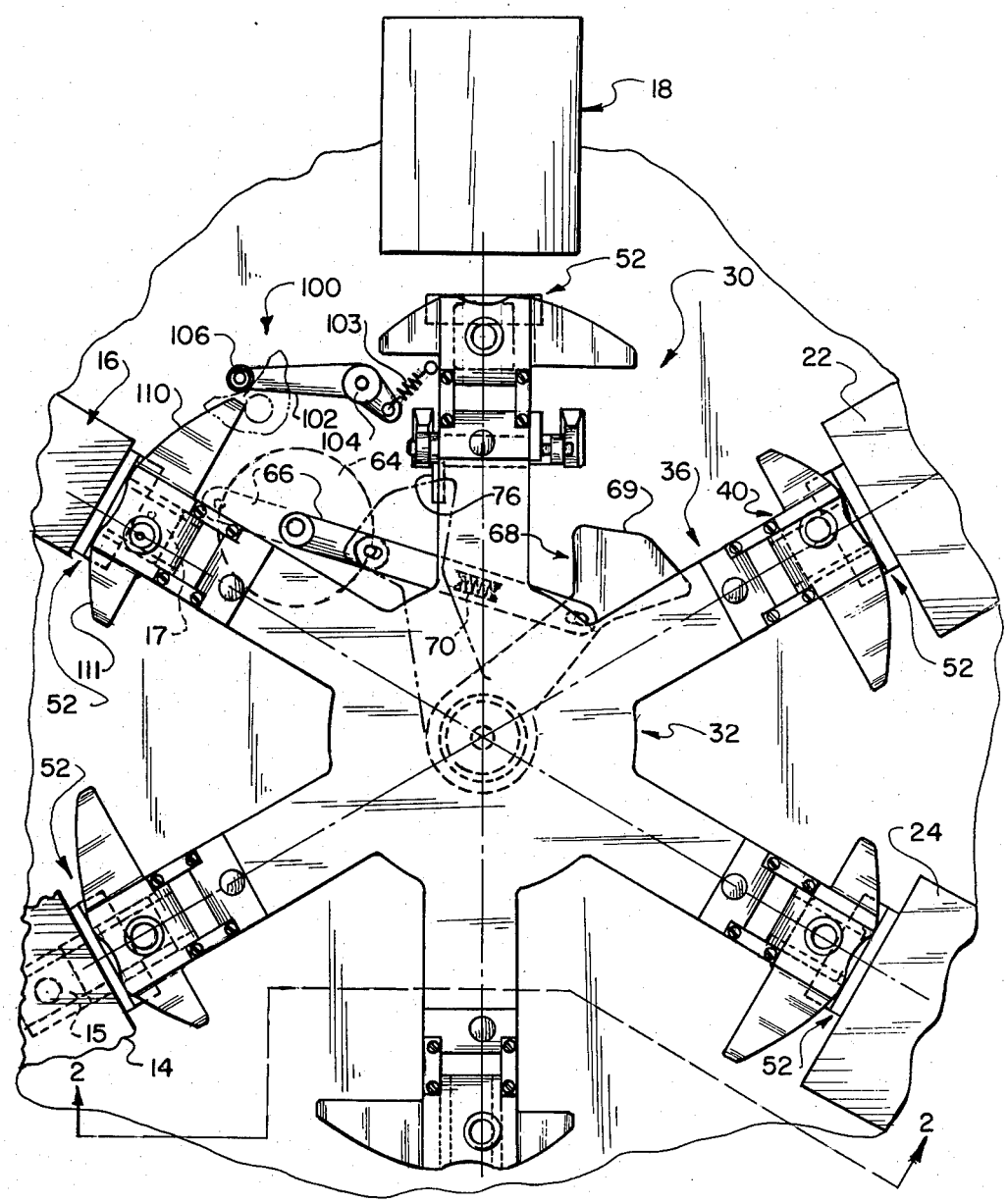
FIG. 3 is a top plan view of the slide distributor.
Figure 4:
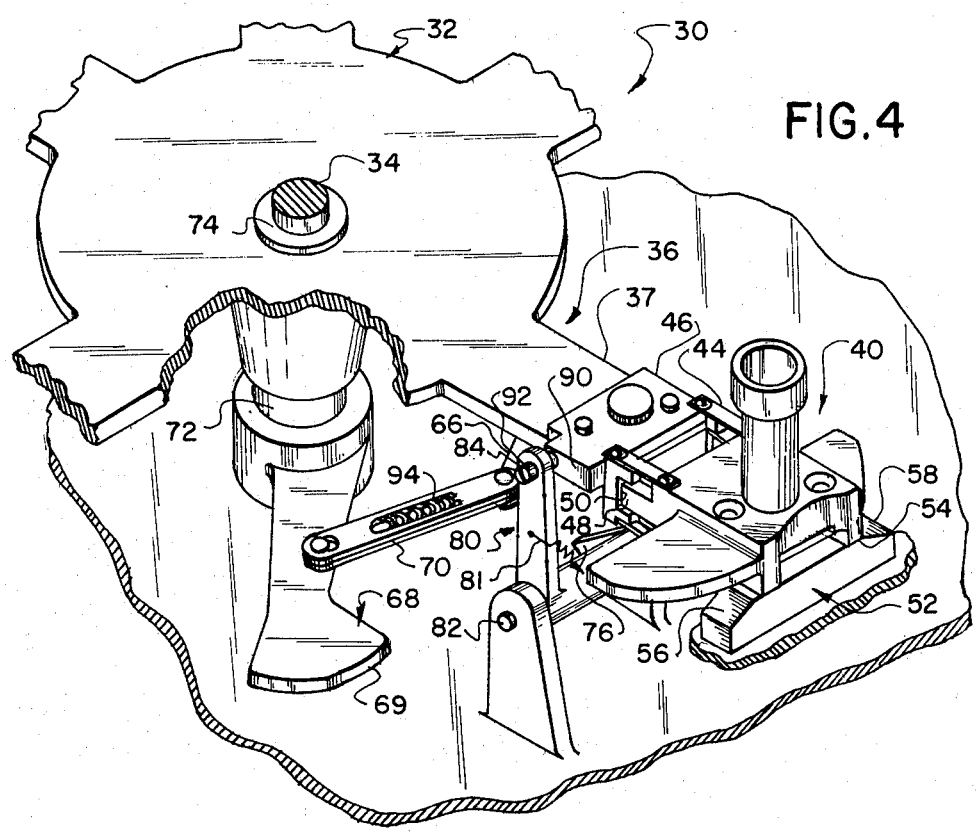
FIG. 4 is a fragmentary perspective view, partially in section, of the slide distributor.

Slide distributor 30, as shown in FIGS. 2–4, comprises a slide transfer means in the form of a rotor 32 journaled on a shaft 34. Rotor 32 comprises six radially-extending arms 36. Each of the arms 36 carries a slide holder 40 which is connected to arm 36 by means of four thin flexure members 44; members 44 are fixed to a connecting block 46 carried on an outer radial end 37 of arm 36. Slide holder 40 has a pair of tabs 48 which are vertically movable within grooves 50 in connecting block 46, the width of grooves 50 defining the limits of vertical movement of slide holder 40. Each of the slide holders 40 is dedicated to either an analysis slide 15 of the colorimetric type or an analysis slide 17 of the potentiometric type. As shown in FIG. 3, a slide holder 40 for receiving analysis slides 15 is shown adjacent slide supply 14, and a slide holder 40 for receiving potentiometric slides is shown adjacent slide supply 16.

Figure 5:
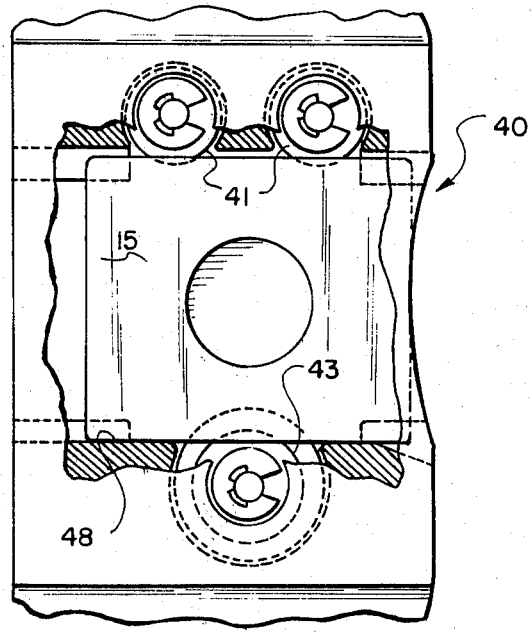
FIG. 5 is a top plan view of the slide holder, with parts broken away to show a slide in the holder.
Figure 6:
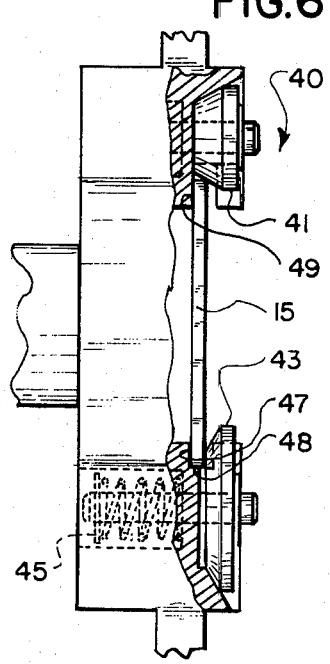
FIG. 6 is an elevational view of the slide holder, rotated 90 degrees from the normal operating position, and with parts broken away to show the rollers for releasably retaining a slide in the holder.

With reference to FIG. 4, each of the slide holders 40 comprises a slot 42 for receiving a slide 15 during the transfer and processing of the slide. As shown in FIGS. 5 and 6, a pair of tapered rollers 41 are located on one side of slot 42, and a tapered roller 43 is located on an opposite side. Rollers 41 and 43, are spring loaded by means of springs 45. A slide 15 in holder 40 will be biased against top surfaces 47, 49, of slot 42 (FIG. 6) by rollers 41 and 43. Slide 15 will also be positioned against surface 48 by rollers 41. Thus, slide 15 will be precisely located laterally and vertically within holder 40. Slot 42 extends through holder 40 such that if a new slide 15 is inserted in a slot 42 which contains a slide 15, the new slide will simply push the slide in holder 40 on through, and no jam will occur. Slide 15 is positioned radially, within slot 42 by a roller mechanism 100, described below.

The analyzer elements which interface with slide distributor 30, i.e. slide supply 14, slide supply 16, metering device 18, and incubators 22, 24, are formed as modules which can be readily removed and installed in analyzer 12. The analyzer elements are arranged adjacent a generally horizontal, circular slide path traced by a slide in slide holder 40, and at each of the analyzer elements is a locating means for slide holder 40 which includes a ramp 52. Ramp 52 comprises a generally horizontal portion 54 and inclined portions 56, 58, on opposite sides of horizontal portion 54. As will be explained in more detail hereinafter, slide holder 40 is adapted to ride on ramp 52 at each of the analyzer elements to vertically locate holder 40 in a direction perpendicular to the slide path. Ramp 52 is preferably formed from a material having a low coefficient of friction, such as acetal, sold under the trademark Delrin.

Rotor 32 is driven in a clockwise direction, as viewed in FIG. 4. As one of the slide holders 40 approaches an analyzer element, e.g. metering device 18, the slide holder 40 will engage and ride up inclined portion 58 of a ramp 52, and the holder 40 will be stopped on horizontal portion 54 of ramp 52. Since each ramp 52 is accurately located on the analyzer element, a slide holder 40 resting on a ramp 52 will always be located in the same vertical position relative to an analyzer element. Upon completion of an operation at a particular analyzer element, holder 40 will be advanced past inclined portion 56 and onto the next element.

Rotor 32 is driven by a rotor drive means 60, as shown in FIGS. 2-4. Drive means 60 comprises a motor 64 (FIG. 3) which is adapted to rotate a crank 66 in a counterclockwise direction, as viewed in FIG. 3. Crank 66 is connected to compressible link 70 which is fixed to a rotor advance lever 68. Rotor advance lever 68 is supported by one-way clutch bearing 72. In each slide advance cycle, rotor 32 is advanced through an angular distance of 60 degrees. The position of rotor 32 at the completion of a slide-advance cycle is shown in FIG. 3; it will be seen that a slide holder 40 is located to cooperate with each of the analyzer elements after each slide-advance cycle.

At the start of a slide-advance cycle, crank 66 moves rotor advance lever 68 in a counterclockwise direction (See FIGS. 3 and 4). Rotor 32 does not rotate during initial movement of lever 68, since it is held by a one-way clutch bearing 74 which prevents movement of rotor 32 in a counterclockwise direction, as viewed in FIG. 4. As rotor advance lever 68 continues the counterclockwise movement, a cam surface 69 on lever 68 engages a projection 76 on a stop bar 80 which is pivotally mounted at 82. The action of cam surface 69 on projection 76 will cause end 84 of stop bar 80 to be pivoted out of the path of connecting block 46 against the action of a return spring, indicated diagrammatically at 81.

As crank 66 is rotated counterclockwise through a top-dead-center position (dotted lines in FIG. 3), the rotor advance lever 68 is reversed and begins to rotate clockwise which in turn causes rotor 32 to rotate clockwise due to the engagement of one-way clutch 72. As crank 66 rotates toward the bottom-dead-center position (solid lines in FIG. 3), the rotor advance lever 68 disengages from projection 76, permitting spring 81 to return stop bar 80 to an upright position, as viewed in FIG. 4. Before crank 66 reaches the bottom-dead-center position, a face 90 of the next connecting block 46 will come into contact with an adjustable stop screw 92 in bar 80. The rotor 32 has thus been rotated 60 degrees and is held rigidly in position by bar 80. Continued movement of crank 66 to the bottom-dead-center position is possible, after rotor 32 is stopped, due to a spring 94 in link 70 which permits connecting link 70 to become compressed.

As will be apparent from the above description, analysis slides 15 are precisely located vertically and circumferentially at the analyzer elements. An analysis slide 15 is located vertically by the interaction of ramp 52 and slide holder 40, and the slide is located circumferentially by means of stop bar 80.

A roller mechanism 100 is provided to locate an analysis slide 15 radially, prior to moving the analysis slide 15 into the metering position. Roller mechanism 100 is shown in FIG. 3 and comprises a bell crank 102 pivotally mounted at 104. Bell crank 102 includes a roller 106 which is adapted to engage an analysis slide 15 held in a slide holder 40 to seat the analysis slide 15 in the holder in the desired radial position. Bell crank 102 is biased by spring 103 into a rest position, not shown. Slide holder 40 includes a fin 110 which is adapted to guide roller 106 into contact with a slide in holder 40 and a fin 111 which is adapted to guide roller 106 to a rest position.

In the operation of slide distributor 30, an analysis slide 15 is fed into a slide holder 40 by a mechanism, not shown, in slide supply module 14. Rotor 32 is then rotated to move the slide 15 into the metering position adjacent metering device 18. After a predetermined amount of fluid has been deposited on the slide 15, rotor 32 is advanced to position slide holder 40 adjacent incubator 22. In this position, a slide ejecting mechanism 120 (FIG. 2) is adapted to remove the slide from slide holder 40 and deposit the slide in incubator 22. It will be understood that an analysis slide 17 of the potentiometric type is processed in the same manner as slide 15.

Rotor drive means 60 is actuated to move slide distributor 30 through a slide advance cycle in timed relation to the other elements of analyzer 12. A control system for drive means 60, as well as for other functions of the analyzer could include a computer, not shown, which may take any of the various forms known in the art that include programmable microcomputers. The instructions and method of programming such computers is well known in the art, and thus, no further explanation is considered necessary.

From the foregoing description, it will be apparent that applicants have disclosed unique apparatus for precisely locating a slide transfer means and an analysis slide therein relative to the various elements of an analyzer. The disclosed apparatus is particularly advantageous for use with modular elements in an analyzer in that the modular elements can be replaced in the analyzer without the necessity for elaborate alignment procedures.

The invention has been defined in detail with reference to certain preferred embodiments thereof, but it will be understood that variations and modifications can be effected within the spirit and scope of the invention.

What is claimed is:

1. Apparatus for use in measuring a characteristic of a sample fluid wherein the fluid is deposited on an analysis slide which is analyzed after an appropriate period of time, said apparatus comprising:

a plurality of apparatus elements, said elements being arranged in a preselected sequence along a path traveled by said slide in said apparatus, said elements including slide supply means, metering means for depositing a predetermined quantity of sample on a slide supported in a metering position, and incubator means;

slide transfer means for moving a slide from said slide supply means along said slide path and for delivering a slide to a selected one of said elements;

drive means for moving said slide transfer means through a series of slide advance cycles; and locating means engageable with said slide transfer means for precisely positioning said slide transfer means and a slide therein relative to each of said elements after each advance cycle to facilitate the processing of the slides and the transfer of slides between said elements and said transfer means.

2. Apparatus, as defined in claim 1, wherein said slide transfer means comprises slide holder means supported for movement within preselected limits along a line perpendicular to said path, and said locating means is adapted to move said holder means within said limits to precisely locate the slide holder means along said line.

3. Apparatus, as defined in claim 2, wherein said locating means comprises ramp means, and said slide holder means is movable within said limits by engagement with said ramp means.

4. Apparatus, as defined in claim 2, wherein said slide transfer means comprises rotor means having a radially-extending arm, and said slide holder means is connected to said arm by flexure means.

5. Apparatus, as defined in claim 4, wherein said rotor means comprises a plurality of said arms and each of said arms includes a slide holder means, and said rotor means includes at least as many arms as there are elements in the apparatus.

6. Apparatus, as defined in claim 4, wherein said locating means comprises a stop means operable on said rotor means to limit the movement thereof to a predetermined angular distance.

7. A slide distributor for use in an analyzer of the type in which a fluid is metered onto an analysis slide which is analyzed after an appropriate period of time, said analyzer including a plurality of modular elements arranged along a slide path, said mechanism comprising:

slide transfer means for receiving a slide from a slide supply means and for moving the slide along said path during a slide advance cycle; said slide transfer means including slide holder means for releasably retaining a slide, said slide holder means being mounted for generally perpendicular movement relative to said path; and locating means for positioning said slide transfer means and a slide therein relative to said elements to facilitate the transfer of slides between the slide transfer means and the elements, said locating means including means at each of said elements for effecting movement of the slide holder means.

8. A slide distributor, as defined in claim 7, wherein said slide transfer means comprises rotor means having a radially-extending arm, said slide holder means is fixed to an outer end of said arm, and rotor drive means is adapted to advance said arm in predetermined angular increments.

9. A slide distributor, as defined in claim 8, wherein said rotor means comprises a plurality of said arms each of which includes a slide holder means, and a stop means is operable on said rotor means to position the rotor in a circumferential position.

10. A slide distributor, as defined in claim 9, wherein said rotor drive means comprises a rotor-advance lever, and said rotor advance lever is adapted to disengage the stop means at the start of said slide advance cycle.

11. In a chemical analyzer for measuring a characteristic of a fluid, the combination comprising:

slide supply means for receiving at least one stack of slides, each slide including means to effect the analysis of a fluid;

sample supply means for receiving a plurality of containers of fluids to be analyzed;

metering means for depositing a predetermined quantity of fluid onto a slide supported in a metering position;

incubator means for providing a controlled environment for slides bearing said fluid;

slide transfer means for receiving a slide from said stack, moving the slide to said metering position, and delivering the slide to said incubator means;

drive means for advancing said slide transfer means in predetermined increments; and locating means engageable with said slide transfer means for precisely positioning said slide transfer means and a slide therein relative to said supply means, said metering means, and said incubator means to facilitate the transfer of slides into and out of said slide transfer means.

12. The combination, as defined in claim 11, wherein said slide transfer means comprises a rotor having a plurality of radially-extending arms, and said drive means is adapted to advance said rotor in predetermined angular increments.

13. The combination, as defined in claim 11, wherein said slide transfer means comprises slide holder means adapted to releasably retain a slide during movement through the analyzer, said slide holder means having a slot for receiving a slide, and bias means is provided in said slot to position and retain the slide therein.

14. The combination, as defined in claim 11, wherein said locating means includes roller means for precisely positioning a slide along the radius of said rotor, said roller means being adapted to engage a slide in said slide transfer means.

* * * * *